US012773570B2

(12) United States Patent
Ring et al.

(10) Patent No.: US 12,773,570 B2
(45) Date of Patent: Oct. 27, 2026

(54) EEG BASED MULTI-FREQUENCY STIMULATION

(71) Applicant: Wave Neuroscience, Inc., Newport Beach, CA (US)

(72) Inventors: Alexander Ring, Newport Beach, CA (US); James William Phillips, Fountain Valley, CA (US)

(73) Assignee: Wave Neuroscience, Inc.

( * ) Notice: Subject to any disclaimer, the term of this patent is extended or adjusted under 35 U.S.C. 154(b) by 982 days.

(21) Appl. No.: 18/002,482

(22) PCT Filed: Jun. 21, 2021

(86) PCT No.: PCT/US2021/038302
§ 371 (c)(1),
(2) Date: Jul. 9, 2023

(87) PCT Pub. No.: WO2021/258068
PCT Pub. Date: Dec. 23, 2021

(65) Prior Publication Data

US 2024/0108909 A1 Apr. 4, 2024

Related U.S. Application Data

(60) Provisional application No. 63/041,401, filed on Jun. 19, 2020.

(51) Int. Cl.

| | |
|---|---|
| ***A61N 2/00*** | (2006.01) |
| ***A61B 5/374*** | (2021.01) |
| ***A61N 1/36*** | (2006.01) |
| ***A61N 2/02*** | (2006.01) |

(52) U.S. Cl.
CPC .............. *A61N 2/006* (2013.01); *A61B 5/374* (2021.01); *A61N 1/36025* (2013.01); *A61N 1/36031* (2017.08); *A61N 1/36034* (2017.08); *A61N 2/02* (2013.01)

(58) Field of Classification Search
CPC .................................................. A61N 2/00–12
See application file for complete search history.

(56) References Cited

U.S. PATENT DOCUMENTS

| | | | | |
|---|---|---|---|---|
| 9,308,385 | B2 | 4/2016 | Jin | |
| 2004/0002635 | A1 | 1/2004 | Hargrove et al. | |
| 2011/0307029 | A1* | 12/2011 | Hargrove ........... | A61N 1/36025 607/45 |
| 2013/0267760 | A1 | 10/2013 | Jin | |
| 2015/0018706 | A1* | 1/2015 | Segal ....................... | A61N 2/02 600/13 |
| 2017/0165496 | A1 | 6/2017 | Pilla et al. | |
| 2018/0256912 | A1* | 9/2018 | Leuchter ................ | A61N 2/006 |
| 2019/0308029 | A1 | 10/2019 | Ho | |
| 2021/0128917 | A1 | 5/2021 | Phillips et al. | |

FOREIGN PATENT DOCUMENTS

| | | | |
|---|---|---|---|
| WO | 2020121274 | A1 | 6/2020 |
| WO | 2021258068 | A1 | 12/2021 |

* cited by examiner

*Primary Examiner* — Thaddeus B Cox
(74) *Attorney, Agent, or Firm* — K&L Gates LLP; Brian J. Novak; Hal Gibson

(57) ABSTRACT

Described are methods and devices for modulating the brain activity of a person using stimulation pulses, where the pulse amplitude is variable and approximates a sine-wave. This results in a stimulation pulse that comprises energy at multiple frequencies.

18 Claims, 3 Drawing Sheets

EEG BASED MULTI-FREQUENCY STIMULATION

PRIORITY CLAIM

This application claims priority to U.S. Provisional Patent Application Ser. No. 63/041,401, filed Jun. 19, 2020, and PCT International Application Number PCT/US2021/038302, filed Jun. 21, 2021 both of which are incorporated by reference herein in their entirety.

BACKGROUND OF THE INVENTION

Repetitive Transcranial Magnetic Stimulation (rTMS) and transcranial Alternating Current Stimulation (tACS) have been used to improve symptoms of mental disorders and to modify brain function. rTMS uses high energy magnetic pulses from a magnetic field generator that is positioned close to a person's head, so that the magnetic pulses affect a desired treatment region within the brain. tACS uses electric current pulses delivered to the scalp. Traditionally, the rTMS or tACS pulses are generated at a fixed frequency for a short time duration. For example, a typical rTMS system may generate pulses at 10 Hz for a duration of 5 seconds. A series of pulses generated over a period of time is referred to as a pulse train. An rTMS treatment session may be composed of several pulse trains, with a rest period between each pulse train. A typical rest period may be 55 seconds, such that 5 seconds of rTMS pulses are generated per minute.

Research has shown that the frequency content of energy pulses delivered to the brain have varying effect on brain function. For example, an article by J. Li and others in 2016 confirmed that low-frequency rTMS pulses can decrease the activity of cortical neurons, whereas high-frequency rTMS can increase the excitability of cortical neurons. They showed varying benefit for recovery of upper limb motor function following a stroke. Two separate articles by Eche et al. in 2012 and Conca et al. in 2002 described using a similar low- and high-frequency stimulation technique to treat major depression, showing positive results. An article by Long et al. in 2018 described combining both high- and low-frequency rTMS, and showed benefit for upper limb motor function in stroke. These articles are incorporated by reference in their entirety herein. Conventionally, low-frequency pulses are about 1 Hz, and high-frequency pulses are set at about 10 Hz.

When delivering combined low and high frequency stimulation to a subject, the most common technique is to provide rTMS or tACS with pulses at a high frequency, followed soon thereafter with stimulation pulses at a low frequency, or vice versa, such as described by an article in 2006 by Fitzgerald et al. Although this technique accomplishes the goal of multi-frequency stimulation, it has several disadvantages, in that stimulation takes longer to perform, and any combinatorial effects are lessened due to the sequential nature of the pulses. Another common technique is to provide bursts of high frequency pulses, where the burst interval is chosen to match a desired low frequency. One example of this is intermittent theta-burst stimulation, in which a short 3-pulse burst at 50 Hz is delivered every 200 milliseconds (i.e., 5 Hz). The resulting waveform comprises significant energy at both 50 Hz and 5 Hz. However, most of the energy occurs at other frequencies, including harmonics of both 5 Hz and 50 Hz.

SUMMARY

The present invention relates to methods and devices to modulate brain activity with repetitive transcranial magnetic stimulation (rTMS) or transcranial Alternating Current Stimulation (tACS) wherein the rTMS or tACS pulse amplitude is variable. The pulse amplitude may be or approximate an alternating waveform. Preferably, the alternating waveform is sinusoidal. Waveforms other than sinusoidal may be used. Examples include square, triangular, and sawtooth. However, other waveforms include frequency content that is not specific to the intrinsic frequency of the alternating waveform, and therefore may reduce the selectivity or efficiency of the resulting stimulation pulse train. For all further examples, a sinusoidal frequency is assumed.

An exemplary embodiment includes modulating brain activity of a subject, comprising: subjecting the subject to repetitive current or magnetic pulses, wherein a pulse frequency is set to or about a first target frequency, and pulse amplitude is variable to approximate a sinusoidal signal comprising a second target frequency and a target amplitude; and improving a physiological condition or a neuropsychiatric condition of the subject. Exemplary embodiments may also include modulation about a target frequency, say 10.5 Hz, with modulation of delivered pulses about the target frequency. Such an application of stimulation energy may provide a wider frequency envelope, such as 10 Hz to 11 Hz. This wider frequency envelope may provide a more complicated combinational spectrum with sinusoidal modulation.

The pulse frequency and the sinusoidal frequency may be chosen to accomplish specific neuromodulation goals, and may be derived from physiologic signals, or may both be preset. In one example, the first target frequency and/or second target frequency is a non-EEG biological metric, or a harmonic or sub-harmonic of said non-EEG biological metric. In another example, first target frequency and/or second target frequency is an existing frequency in the EEG band, or a harmonic or sub-harmonic of an intrinsic frequency within a specified EEG band. Other options exist for the first and/or second target frequency.

In an exemplary embodiment, the pulse frequency may be set to the first target frequency. The sinusoidal frequency may be set to a second target frequency. It has been shown that stimulation that is at a harmonic of the heart rate may be beneficial, as well as stimulation at the subject's alpha frequency. In one example, the first target frequency is about an intrinsic frequency within an alpha band of the subject, and the second target frequency is about a resting heart rate of the subject.

Neuromodulation may use many different forms. Any type of stimulation that can be administered in varying amplitude pulses would be a good candidate for use with the present invention. In one example using tACS, the current pulses are generated using transcranial alternating current stimulation. In another example using rTMS, the magnetic pulses are generated using repetitive transcranial magnetic stimulation.

The present invention may be used to treat a number of physiological or neuropsychiatric conditions. Any condition where a combination of low and high frequency pulsed stimulation would benefit is a possible candidate. In one example, the neuropsychiatric condition is Autism Spectrum Disorder (ASD), Alzheimer's disease, ADHD, schizophrenia, anxiety, depression, coma, Parkinson's disease, substance abuse, bipolar disorder, a sleep disorder, an eating disorder, tinnitus, traumatic brain injury, mild cognitive impairment, post-traumatic stress syndrome, or fibromyalgia.

To implement the method of the present invention, a device may be designed to specifically multiply a sine wave and pulse train together to create a pulse train of varying sinusoidal amplitude. This may be used to either drive a rTMS coil or stimulate through electrodes, or conductive material.

In one example using rTMS, a device is specified for applying a varying magnetic field to a head of a subject, the device comprising: a sine-wave generator which creates a sinusoidal signal having a sinusoidal amplitude and sinusoidal frequency; and a pulse timing generator which creates a pulse timing signal having a pulse frequency; and a driver circuit configured to provide a voltage or current output at an amplitude that is proportional to the sinusoidal amplitude at a time specified by the pulse frequency; and a magnetic field generator which generates a magnetic field with an amplitude proportional to the current or voltage output from the driver circuit. The pulse frequency and sinusoidal frequencies may be fixed or based on biological metrics including EEG. In one rTMS example, the pulse frequency is a non-EEG biological metric, or a harmonic or sub-harmonic of said non-EEG biological metric of a subject. In another rTMS example, the pulse frequency is an existing frequency in the EEG band, a harmonic or a sub-harmonic of an intrinsic frequency within a specified EEG band of a subject. In another rTMS example, the sinusoidal frequency is a non-EEG biological metric, or a harmonic or sub-harmonic of said non-EEG biological metric of a subject. In another rTMS example, the sinusoidal frequency is an existing frequency in the EEG band, a harmonic or a sub-harmonic of an intrinsic frequency within a specified EEG band of a subject. In another rTMS example, the pulse frequency is about an intrinsic frequency within an alpha band of the subject, and the sinusoidal frequency is about a resting heart rate of the subject. In another rTMS example, the pulse frequency and the sinusoidal frequency are fixed values and the value of the pulse frequency is greater than the value of the sinusoidal frequency. In another rTMS example, the value of the pulse frequency is about 10 Hz and the value of the sinusoidal frequency is about 1 Hz.

In one example using tACS, a device is specified for applying a varying electric current to a head of a subject, the device comprising: a sine-wave generator which creates a sinusoidal signal having a sinusoidal amplitude and sinusoidal frequency; and a pulse timing generator which creates a pulse timing signal having a pulse frequency; and a driver circuit configured to provide a voltage or current output at an amplitude that is proportional to the sinusoidal amplitude at a time specified by the pulse frequency; one or more electrodes, which are configured to provide electric current or voltage to the head of the subject with an amplitude proportional to the current or voltage output from the driver circuit. The pulse frequency and sinusoidal frequencies may be fixed or based on biological metrics or EEG metrics. In one tACS example, the pulse frequency is a non-EEG biological metric, or a harmonic or sub-harmonic of said non-EEG biological metric of a subject. In another tACS example, the pulse frequency is an EEG metric, a harmonic or a sub-harmonic of an intrinsic frequency within a specified EEG band of a subject. In another tACS example, the sinusoidal frequency is a non-EEG biological metric, or a harmonic or sub-harmonic of said non-EEG biological metric of a subject. In another tACS example, the sinusoidal frequency is an EEG metric, a harmonic or a sub-harmonic of an intrinsic frequency within a specified EEG band of a subject. In another tACS example, the pulse frequency is about an intrinsic frequency within an alpha band of the subject, and the sinusoidal frequency is about a resting heart rate of the subject. In another tACS example, the pulse frequency and the sinusoidal frequency are fixed values and the value of the pulse frequency is greater than the value of the sinusoidal frequency. In another tACS example, the value of the pulse frequency is about 10 Hz and the value of the sinusoidal frequency is about 1 Hz.

BRIEF DESCRIPTION OF THE DRAWINGS

A better understanding of the features and advantages of the devices and methods provided will be obtained by reference to the following detailed description that sets forth illustrative embodiments and the accompanying drawings of which.

DETAILED DESCRIPTION

Figure 1:
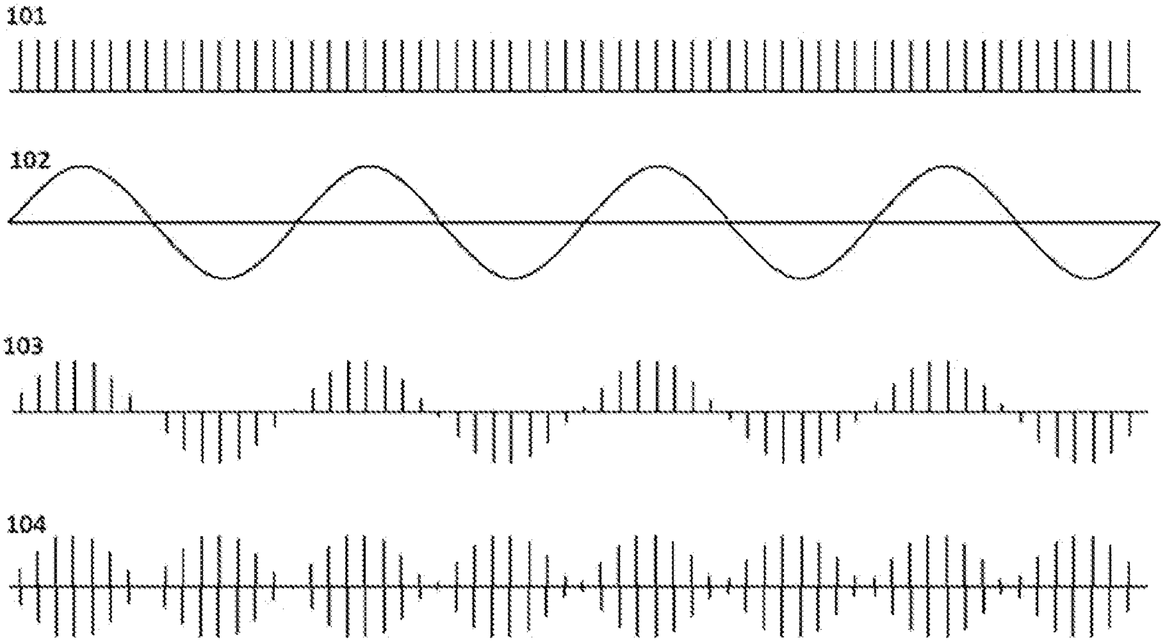
FIG. 1 shows an exemplary pulse train multiplied by a sine-wave. The figure shows the output from a mono-phasic pulse stimulator and a bi-phasic pulse stimulator.

While certain embodiments have been provided and described herein, it will be readily apparent to those skilled in the art that such embodiments are provided by way of example only. It should be understood that various alternatives to the embodiments described herein may be employed, and are part of the invention described herein.

Conventionally, multiple frequency stimulation using rTMS or tACS is accomplished by setting a pulse frequency to a first target frequency and providing stimulation, followed by stimulation using a pulse frequency set to a second target frequency. The present invention allows stimulation pulses with energy at two or more separate frequencies provided concurrently.

Exemplary embodiments described herein include systems and methods for administering stimulation energy to a patient at multiple frequencies simultaneously or concurrently. Exemplary embodiments of methods may combine more than one signal together to generate a pulse train with amplitude variation which approximates an alternating waveform. Preferably, the alternating waveform is sinusoidal. Waveforms other than sinusoidal may be used. Examples include square, triangular, and sawtooth. However, other waveforms include frequency content that is not specific to the intrinsic frequency of the alternating waveform, and therefore may reduce the selectivity or efficiency of the resulting stimulation pulse train. For all further examples, a sinusoidal frequency is assumed. The pulse train may be monophasic or biphasic. To implement the method of the present invention, a device may be designed to specifically multiply a sine wave and pulse train together to create a pulse train of varying sinusoidal amplitude. This may be used to either drive a rTMS coil or stimulate through electrodes.

Using a Fourier Transform, it can be seen that the frequency spectrum of a pulse train is a series of pulses in the frequency domain, occurring at all harmonics of the pulse frequency. For example, a 10 Hz series of pulses transforms to a series of pulses in the frequency domain occurring at all integer multiples of 10 Hz ( . . . , −20 Hz, −10 Hz, 0 Hz, 10 Hz, 20 Hz, . . . ). The frequency spectrum of a sinusoid of a specified sinusoidal frequency consists of two pulses in the frequency domain occurring at the positive and negative values of the sinusoidal frequency. For example, a 1 Hz sinusoid transforms to pulses at +/−1 Hz in the frequency domain.

When two signals are multiplied together in the time domain, the resulting frequency spectrum consists of the convolution of the frequency spectrum of the two signals together. Therefore, by multiplying a sine wave with a pulse train, it is possible to provide stimulation energy at multiple frequencies concurrently. For example, if a 1 Hz sine wave is multiplied with a 10 Hz pulse train, the resulting frequency spectrum consists of pulses at multiple frequencies ( . . . , −21 Hz, −19 Hz, −11 Hz, −9 Hz, −1 Hz, 1 Hz, 9 Hz, 11 Hz, 19 Hz, 21 Hz, . . . ).

It has been shown that stimulation that is at a harmonic of the heart rate may be beneficial, as well as stimulation at the subject's alpha frequency. In one example, exemplary embodiments may include a first target frequencies at about an intrinsic frequency within an alpha band of the subject, and a second target frequency at about a resting heart rate of the subject.

A method of setting the target frequencies, from an implementation standpoint, is to keep the frequencies fixed. In an exemplary embodiment, the sinusoidal frequency is less than or equal to half of the pulse frequency. This would cause the frequency spectrum of the signal after multiplication of the pulse train with the sine-wave to become aliased, in which pulses may not occur at distinct frequency values. Therefore, it is generally desirable for the first target frequency of the pulse frequency to be at least twice the second target frequency of the sinusoidal frequency. In one example, the first target frequency and the second target frequency are fixed values and the value of the first target frequency is greater than the value of the second target frequency.

Exemplary embodiments may also include modulation about a target frequency, say 10.5 Hz, with modulation of delivered pulses about the target frequency. Such an application of stimulation energy may provide a wider frequency envelope, such as 10 Hz to 11 Hz. This wider frequency envelope may provide a more complicated combinational spectrum with sinusoidal modulation. In an exemplary embodiment, a target frequency may be used with a modulation about 0.1 Hz to 1.0 Hz, such as +/−0.5 Hz or other desired ranges.

Low frequency stimulation is commonly less than 5 Hz, whereas high frequency stimulation is greater than 5 Hz. Two common stimulation pulse frequencies that are used to treat neuropsychiatric disorders is for the low-frequency stimulation to be at 1 Hz and the high frequency stimulation to be at 10 Hz. Therefore, a potential stimulation waveform for the present invention would be to make the sinusoidal frequency equal to 1 Hz and the pulse frequency equal to 10 Hz. In one example, the first target frequency is about 10 Hz and the second target frequency is about 1 Hz.

The term about or approximately may be used herein, such that the value may be equal to the stated value, may be proximate to the stated value, and/or vary around the stated value. Such variation may be based on the normal operational variations of the equipment used to generate a given value. The approximation or expanse of the term "about" or "approximately" may also include variations to achieve the desired therapeutic response. For example, providing a pulse frequency or sinusoidal frequency to either a harmonic of a non-EEG biological metric, or a harmonic of an intrinsic frequency within a specified EEG band may be delivered within +/−1.0 Hz for the treatment to have a desired effect. As such, the term about may include the stated number and be +/−1 Hz around the stated number and be within the desired range. Therapeutic effectiveness may be at other ranges, such as +/−0.5 Hz, and would be understood by a person of skill in the art.

FIG. 1 shows exemplary elements of the method according to embodiments described herein. A pulse train (101) is created. This pulse train comprises a pulse frequency. The pulse frequency may be any value. However, the pulse frequency is preferably kept to a level below the maximum that would be supported by the hardware that provides the stimulation. For example, if the output of stimulation is an rTMS pulse train, the pulse frequency is generally limited by the ability of the charging circuit to generate the current pulse through the coil. For example, the pulse frequency in many rTMS systems may be 100 Hz or less. The pulse amplitude in (101) is not essential, since it is only required to provide timing for the stimulation pulses. A sine-wave (102) is also created. The sine wave comprises a sinusoidal frequency. This frequency may also be any value, but the sinusoidal frequency is preferably equal to or less than ½ the pulse frequency of the pulse train (101). The pulse train samples the sine wave, and therefore the sine wave may be less than half the pulse frequency. If it is not, then aliasing may occur, and the frequency spectrum may not match the desired output. An exemplary monophasic pulse train with sinusoidal amplitude variation is shown in (103). This output is the result of the multiplication of the sine-wave (102) and the pulse train (101). The waveform in (103) may be an rTMS pulse, a tACS pulse, or some other stimulation waveform. For example, the output could be a Transcutaneous Electrical Nerve Stimulation (TENS), ultrasonic stimulation, Pulsed Electromagnetic Field (PEMF) stimulation, Deep Brain Stimulation (DBS), Cortical Electrical Stimulation (CES), peripheral nerve stimulation, or physical stimulation, such as tapping or striking the skin. Any stimulation of a subject which may be accomplished by a sequence of stimulation pulses of varying amplitude could be a candidate for the present invention. In (104), the output is a bi-phasic stimulation pulse train. This is similar to the monophasic pulse train, except that the stimulation pulse is allowed to be both positive and negative.

Figure 2:
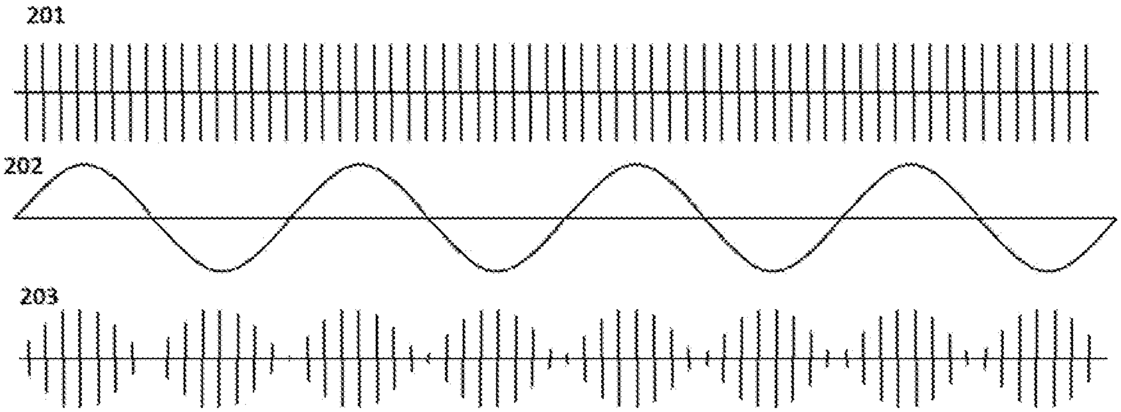
FIG. 2 shows an alternative embodiment in which the pulse train is bi-phasic, so that when it is multiplied by a sine-wave, the output is a bi-phasic pulse stimulator.

FIG. 2 shows an exemplary embodiment of the present invention. Instead of a simple mono-phasic pulse train (101), a bi-phasic pulse train (201) is generated and multiplied by the sine-wave (202), which directly creates a bi-phasic pulse train with sinusoidal varying amplitude (203). This may allow a simpler system, which does not require a special drive circuitry to generate the stimulation pulses.

Figure 3:
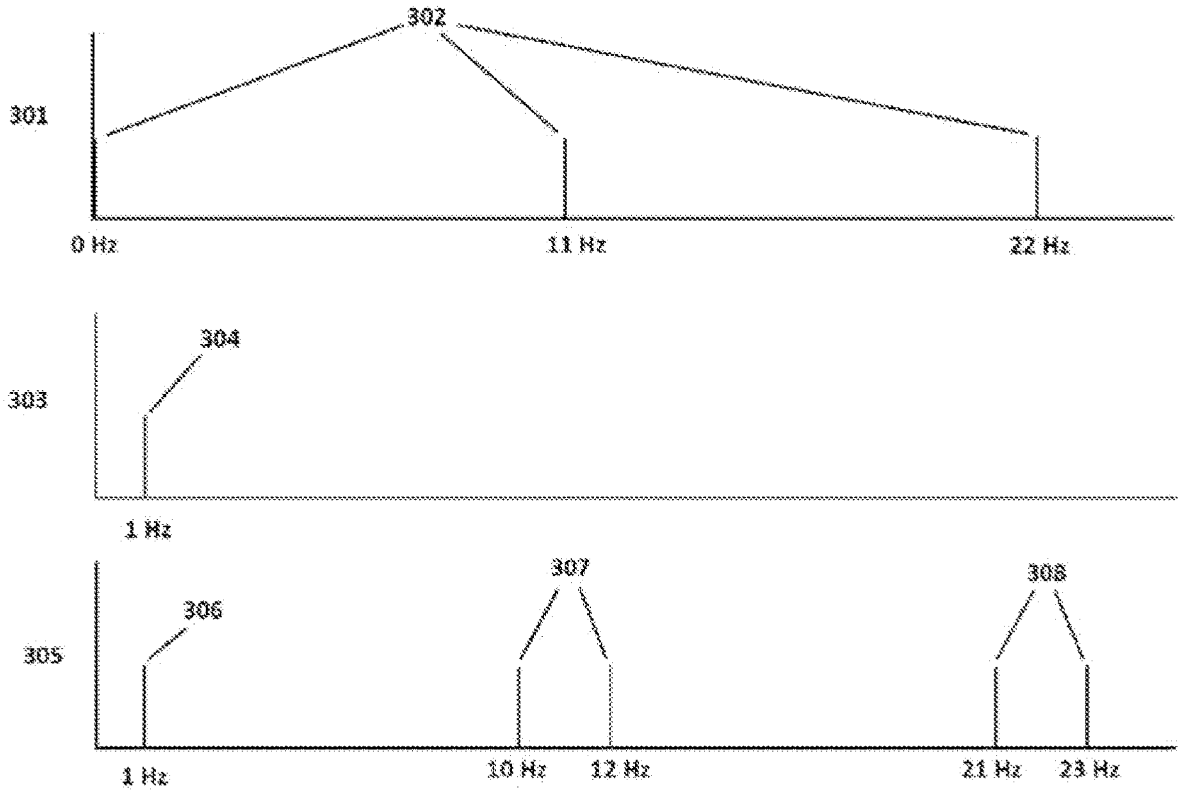
FIG. 3 shows an exemplary frequency distribution for the pulse train, for the sine-wave, and for the two multiplied together.

FIG. 3 shows an exemplary frequency spectrum of signals used in the present invention. Graph (301) shows the frequency spectrum of a pulse train with pulse frequency of 11

Hz. As can be seen, the frequency spectrum (302) is also composed of pulses at harmonics of the pulse frequency. Shown in the figure are pulses at 0 Hz, 11 Hz, and 22 Hz. This spectrum extends on both positive and negative directions. The frequency spectrum of a 1 Hz sine-wave is shown in graph (303), with a single pulse (304) at 1 Hz. Not shown is a second pulse at −1 Hz. When the 10 Hz pulse train and the 1 Hz sine-wave are multiplied together, the frequency spectrums convolve, resulting in the waveform having a frequency spectrum represented in graph (305). The convolution results in pulses at 1 Hz (306), 10 Hz & 12 Hz (307), and 20 Hz & 22 Hz (308). This pattern extends in both the positive and negative direction. The stimulation energy may therefore be administered with a variety of frequencies concurrently through the application of a single pulse train signal to the patient. The single pulse train signal may be generated based on a combination of frequencies as described herein. The single pulse train signal may include a varying amplitude. The varying amplitude of the single pulse train signal may be approximately sinusoidal.

As was mentioned previously, stimulation energy at multiple frequencies may be valuable in treating a number of disorders. In the example of FIG. 3, the main stimulation energy is at 1 Hz and 10 Hz. Often in neuromodulation and brain stimulation, additional energy at alternate frequencies does not reduce the effectiveness of the stimulation at the two primary frequencies. Therefore, the higher frequencies can remain and administered to the patient along with the primary frequencies. They can also be removed or reduced through filtering or other methods. Therefore, these other frequency components that exist and not relevant to treatment maybe reduced through filtering or other methods.

According to embodiments described herein, a method of modulating a brain activity of a subject, includes subjecting the subject to repetitive current or magnetic pulses, wherein a pulse frequency is set to about a first target frequency, and a pulse amplitude is variable to approximate a sinusoidal signal comprising a second target frequency and a target amplitude, and improving a physiological condition or a neuropsychiatric condition of the subject.

The first target frequency and the second target frequency may be fixed values. The value of the first target frequency may be greater than the value of the second target frequency. The value of the first target frequency may be greater than or equal to double the value of the second target frequency. The first target frequency may be about 10 Hz and the second target frequency may be about 1 Hz.

The first target frequency and/or the second target frequency may be a non-EEG biological metric, or a harmonic or sub-harmonic of said non-EEG biological metric. For example, the first target frequency may be a non-EEG biological metric that is closest to the target frequency in a desired EEG band such as, for example, the heart rate, which is a sub-harmonic of the alpha frequency. Other non-EEG biological metrics include the patient's respiratory rate and the gastrointestinal movement rate (rate of peristalsis). Other cyclical non-EEG biological metric may be used.

The first target frequency may be within an intrinsic frequency of a subject within a specific EEG band, and/or a harmonic or sub-harmonic of the intrinsic frequency within a specified EEG band.

In an exemplary embodiment, the first target frequency is about an intrinsic frequency within an alpha band of the subject, and the second target frequency is about a resting heart rate of the subject.

The current pulses may be generated using transcranial alternating current stimulation. The magnetic pulses may be generated using repetitive transcranial magnetic stimulation.

Exemplary embodiments of the system and method described herein may be used to treat a neuropsychiatric condition, such as, without limitation, Autism Spectrum Disorder (ASD), Alzheimer's disease, ADHD, schizophrenia, anxiety, depression, coma, Parkinson's disease, substance abuse, bipolar disorder, a sleep disorder, an eating disorder, tinnitus, traumatic brain injury, post-traumatic stress syndrome, and/or fibromyalgia.

Figure 4:
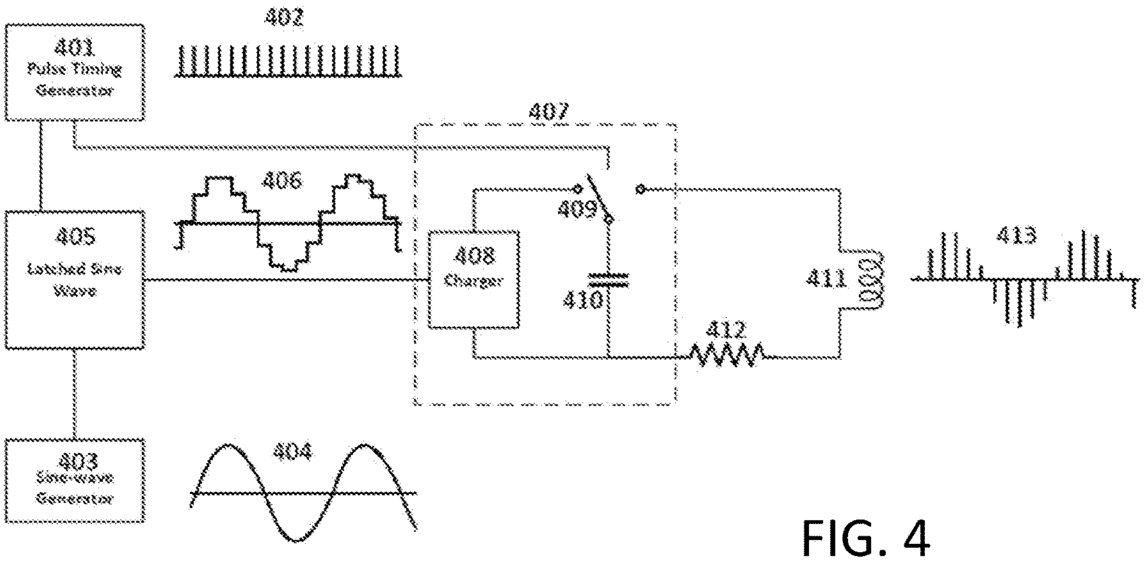
FIG. 4 shows an exemplary device which generates a mono-phasic rTMS stimulation by multiplying a sine-wave with a pulse train and using the output as a desired charge level to drive the rTMS coil.

FIG. 4 shows an exemplary device, which may generate the pulse train with varying sinusoidal amplitude. The output is a train of rTMS pulses. A pulse timing generator (401) creates the pulse train (402) with a specified pulse frequency. This can be implemented using a timer circuit and an amplifier. The signal pulse may be used to specify the timing of the rTMS pulses. Therefore, the signal amplitude may be any quantity. A sine-wave generator (403) creates a sine-wave (404) with a specified sinusoidal frequency. This can be accomplished using an oscillator circuit such as one that uses an inductor and a capacitor (a LC-oscillator circuit), or with a Digital to Analog Converter (DAC).

The latched sine-wave circuit (405) samples the sine-wave at a timing specified by the pulse timing generator, and generates a signal resembling approximately a sinusoidal wave, or step-wise sine wave (406). This circuit provides a charge amplitude for the driver (407), which comprises a charger circuit (408), a switch (409), and a capacitor (410). The charger circuit charges a capacitor (410) to the level specified by the latched sine-wave, during the time interval when the switch changes configuration to form the connection between the Charger circuit and the capacitor. The stimulation pulse timing is controlled by the signal from the pulse timing generator, causing the switch to change configuration and make a connection between the capacitor and a rTMS coil (411) and resistor (412). Depending on how long the switch is activated in a desired configuration, the resulting pulses may be mono-phasic or bi-phasic. The generated pulse train may be selected based on the desired application to the patient. For example, the switch may be only active long enough to generate a mono-phasic rTMS pulse (413), or may be connected for a longer time to generate a bi-phasic pulse.

Figure 5:
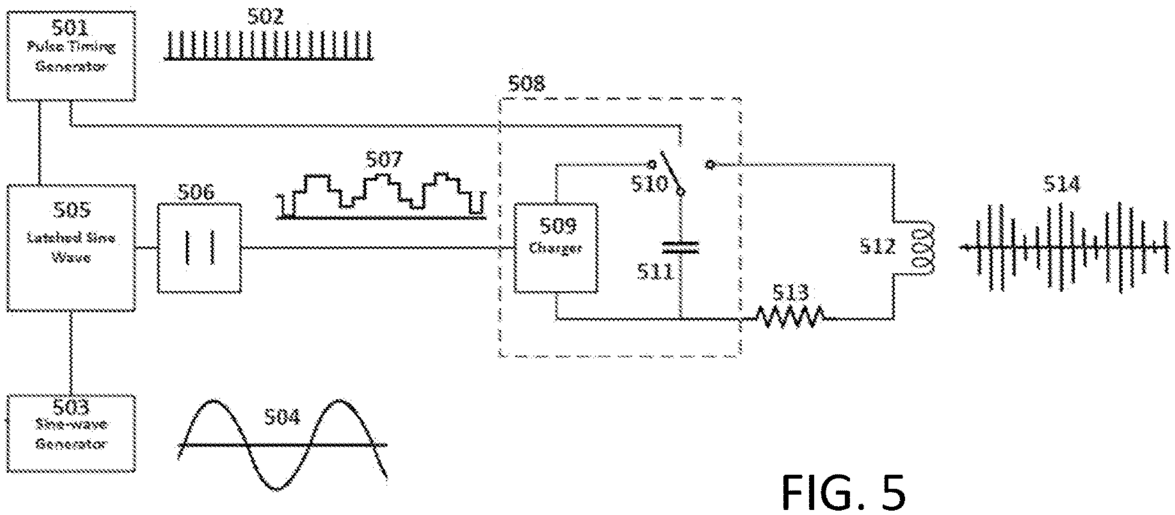
FIG. 5 shows an alternate embodiment in which a bi-phasic rTMS pulse is generated by multiplying a sine-wave with a pulse train and creating a signal which is the magnitude of the output. The driving circuit uses this as a desired charge level and generates a bi-phasic rTMS pulse in which the amplitude of the pulses is sinusoidal.

FIG. 5 shows an exemplary device, which generates a biphasic rTMS stimulation pulse in an alternate way. A pulse train (502) is generated by a pulse timing generator (501) and a sine-wave generator (503) generates a sine-wave (504). The latched sine-wave circuit (505) output is fed through electronic component (506), which generates the magnitude of the latched sine-wave, as can be seen in the step-wise oscillatory signal (507). The driver (508) comprises a charger (509), switch (510), and capacitor (511), which charges the capacitor up to a value, which is always positive. The capacitor value is preferably large enough to administer the desired pulse amplitude through the coil, resulting in an rTMS pulse which can affect brain activity through induction. Typical capacitor values are in the range from 500-1500 micro-farads. This has the advantage that it allows capacitors that can only charge in one polarity, such as an electrolytic capacitor. When the switch (510), flips, the capacitor discharges through the rTMS coil (512) and resistor (513), in order to create a bi-phasic rTMS pulse train with varying amplitude that approximates a sine-wave (514).

Figure 6:
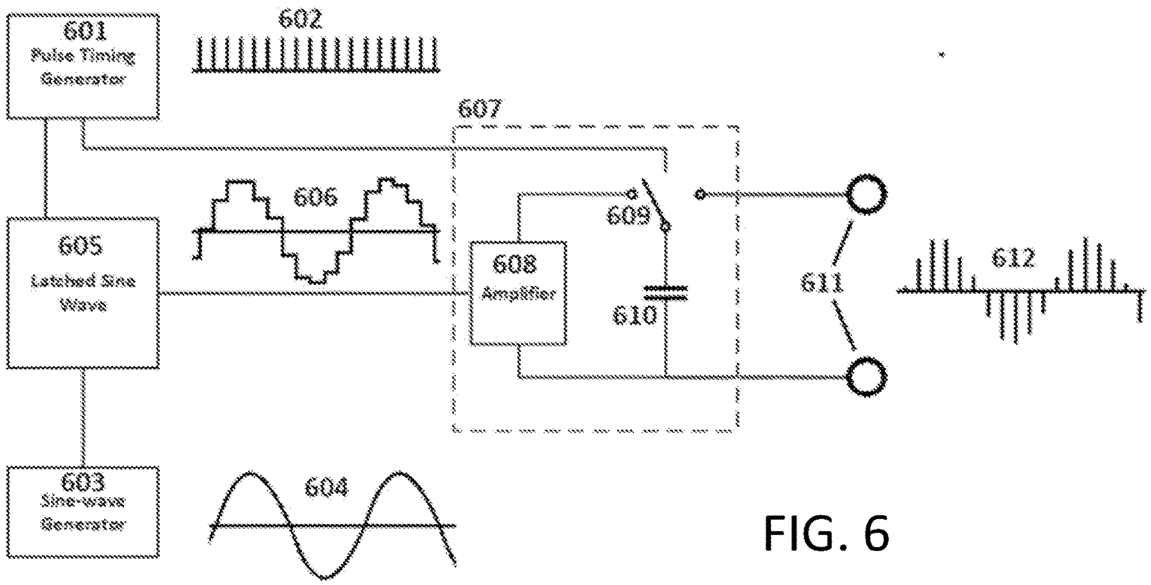
FIG. 6 shows an exemplary device which generates mono-phasic sinusoidal tACS stimulation pulses, in which a sine-wave is multiplied with a pulse train, and the output is used as a target level for an amplifier that charges a capacitor, which discharges at the desired level and time through electrodes.

FIG. 6 shows an exemplary device, which generates a tACS stimulation pulse train with varying sinusoidal pulses. A pulse train (602) is generated by a pulse timing generator (601) and a sine-wave generator (603) generates a sine-wave (604). The latched sine-wave circuit creates the latched sine wave (606) that serves as input to the driver circuit (607). The driver (607) comprises a charger (608), switch (609), and capacitor (610), which charges the capacitor up to a specified value when the pulse train from the pulse timing generator connects the amplifier to the capacitor. When a stimulation pulse is to be generated by the pulse train, the switch changes configuration to connect the capacitor to the subject through two electrodes (611), creating the stimulation pulse train with varying amplitude approximating a sine-wave (612).

A device for applying a varying magnetic field to a head of a subject is described herein. The device may include a sine-wave generator which creates a sinusoidal signal having a sinusoidal amplitude and sinusoidal frequency, and a pulse timing generator which creates a pulse timing signal having a pulse frequency, and a driver circuit configured to provide a voltage or current output at an amplitude that is proportional to the sinusoidal amplitude at a time specified by the pulse frequency, and a magnetic field generator which generates a magnetic field with an amplitude proportional to the current or voltage output from the driver circuit.

Exemplary embodiments may include a device for applying a varying electric current to a head of a subject. The device may include a sine-wave generator which creates a sinusoidal signal having a sinusoidal amplitude and sinusoidal frequency, a pulse timing generator which creates a pulse timing signal having a pulse frequency, a driver circuit configured to provide a voltage or current output at an amplitude that is proportional to the sinusoidal amplitude at a time specified by the pulse frequency, and two electrodes, which are configured to provide electric current or voltage to the head of the subject with an amplitude proportional to the current or voltage output from the driver circuit.

The sinusoidal frequency and/or pulse frequency may be fixed values. The value of the pulse frequency may be greater than the value of the sinusoidal frequency. The value of the pulse frequency may be greater than or equal to double the value of the sinusoidal frequency. The pulse frequency may be about 10 Hz and the sinusoidal frequency may be about 1 Hz.

The sinusoidal frequency and/or pulse frequency may be a non-EEG biological metric, or a harmonic or sub-harmonic of said non-EEG biological metric. For example, the frequency may be a non-EEG biological metric that is closest to the target frequency in a desired EEG band such as, for example, the heart rate, which is a sub-harmonic of the alpha frequency. Other biological metrics include the patient's respiratory rate and the gastrointestinal movement rate (rate of peristalsis). Other cyclical non-EEG biological metric may be used.

The sinusoidal frequency and/or pulse frequency may be within an intrinsic frequency of a subject within a specific EEG band, and/or a harmonic or sub-harmonic of the intrinsic frequency within a specified EEG band.

In an exemplary embodiment, the pulse frequency is about an intrinsic frequency within an alpha band of the subject, and the sinusoidal frequency is about a resting heart rate of the subject.

As exemplary embodiments may set the pulse frequency and/or sinusoidal frequency at parameters related to the subject, the system may be configured to receive and/or determine the target values from the parameters related to the subject. For example, the system may be configured to receive and/or detect an EEG, and/or non-EEG, biological metric of the subject, including, without limitation, EEG, heart rate, the subject's respiratory rate, and the gastrointestinal movement rate (rate of peristalsis), etc. The system may also or alternatively be able to determine a target frequency based on the received and/or detected EEG or non-EEG biological metric. For example, the system may receive and/or determine from the EEG an intrinsic frequency from an alpha band (or other band) of the EEG, a resting heart rate, a frequency of the subject's respiratory rate, and/or a frequency of the subject's gastrointestinal movement rate.

Exemplary embodiments described herein include methods of modulating a brain activity of a subject, including subjecting the subject to repetitive current or magnetic pulses, wherein the repetitive current or magnetic pulses have a pulse frequency at a first target frequency, and a pulse amplitude that is variable to approximate a sinusoidal signal comprising a second target frequency and a target amplitude; and improving a physiological condition or a neuropsychiatric condition of the subject.

The system and methods described herein may include receiving a non-EEG biological metric of the subject and setting the first target frequency at the non-EEG biological metric, or a harmonic or sub-harmonic of the non-EEG biological metric. The method may also or alternatively include receiving an intrinsic frequency within a specific EEG band of the subject and setting the first target frequency at the intrinsic frequency within the specified EEG band, or a harmonic or sub-harmonic of the intrinsic frequency within the specified EEG band.

Exemplary embodiments of the system and method described herein may include receiving a non-EEG biological metric of the subject and setting the second target frequency at the non-EEG biological metric, or a harmonic or sub-harmonic of the non-EEG biological metric of the subject. The system and method may also or alternatively include receiving an intrinsic frequency within a specific EEG band of the subject and setting the second target frequency at the intrinsic frequency within the specified EEG band, or at a harmonic or sub-harmonic of the intrinsic frequency within the specified EEG band of the subject.

The received non-EEG biological metric and/or EEG biological metric may be used as target frequencies for the first and/or second target frequency. The received non-EEG biological metric and/or EEG biological metric as described herein may be determined directly by the system such as by including sensors for detecting a subject's EEG, heart rate, the subject's respiratory rate, and the gastrointestinal movement rate (rate of peristalsis), etc., and then electronics/software (including processor, memory, and machine instructions stored in memory and executed by the processor) for determining the target frequency from the subject's metric. The received non-EEG biological metric and/or EEG biological metric may also or alternatively be through receipt of the information by the system, such as through a wired or wireless communication from another system or entry. This may be from an outside system that has detected and/or determined the metric, and in which the metric is provided to embodiments of the system herein through a data and/or user interface.

Exemplary embodiments of the system and methods described herein may include receiving an intrinsic frequency within an alpha band of an EEG of the subject and setting the first target frequency at about the intrinsic frequency within the alpha band of the subject; and receiving a resting heart rate of the subject and setting the second target frequency at about the resting heart rate of the subject. The receipt of the intrinsic frequency and/or resting heart rate may be as a data entry into the system and/or may be determined directly by the system or another system in communication with the system such as by using sensors and/or algorithms to determine the intrinsic frequency and/or resting heart rate of the subject.

Exemplary embodiments of the system and methods included herein include the first target frequency and the second target frequency being fixed values and the value of the first target frequency is greater than the value of the second target frequency. These fixed values may be set by a user and/or by the system according to embodiments described herein. In an exemplary embodiment the first target frequency is about 10 Hz and the second target frequency is about 1 Hz. The term "about" may be determined based on the normal operating tolerance of the electric or magnetic application of frequencies as would be understood by a person of skill in the art. Such tolerance may be based on the treatment, the protocol, and/or the machine. Exemplary embodiments include tolerances of +/−1 Hz, +/−0.5 Hz, +/−0.1 Hz.

The methods and systems described herein may include subjecting the subject to repetitive current or magnetic pulses comprises subject the subject to current pulses and the current pulses are generated using transcranial alternating current stimulation. The subjecting the subject to repetitive current or magnetic pulses may include providing a device for applying a varying magnetic field, having: a sine-wave generator which creates a sinusoidal signal having a sinusoidal amplitude and sinusoidal frequency, a pulse timing generator which creates a pulse timing signal having a pulse frequency, a driver circuit configured to provide a voltage or current output at an amplitude that is proportional to the sinusoidal amplitude at a time specified by the pulse frequency, and a magnetic field generator which generates a magnetic field with an amplitude proportional to the current or voltage output from the driver circuit; and the method also may include subjecting the subject to repetitive magnetic pulses with the magnetic field generator of the device.

The methods and system described herein may include wherein subjecting the subject to repetitive current or magnetic pulses comprises subjecting the subject to magnetic pulses and the magnetic pulses are generated using repetitive transcranial magnetic stimulation. The system and method may include the subjecting the subject to repetitive current or magnetic pulses comprising: providing a device for applying a varying current, having: a sine-wave generator which creates a sinusoidal signal having a sinusoidal amplitude and sinusoidal frequency, a pulse timing generator which creates a pulse timing signal having a pulse frequency, a driver circuit configured to provide a voltage or current output at an amplitude that is proportional to the sinusoidal amplitude at a time specified by the pulse frequency, and two electrodes, which are configured to provide electric current or voltage to the head of the subject with an amplitude proportional to the current or voltage output from the driver circuit. The method may also include subjecting the subject to repetitive current pulses with the two electrodes of the device.

The systems and methods described herein may be used to treat neuropsychiatric condition that may include any one or more of Autism Spectrum Disorder (ASD), Alzheimer's disease, ADHD, schizophrenia, anxiety, depression, coma, Parkinson's disease, substance abuse, bipolar disorder, a sleep disorder, an eating disorder, tinnitus, traumatic brain injury, post-traumatic stress syndrome, or fibromyalgia.

The description herein is generally in terms of treatment of a person. However, the disclosure is not so limited but may be applicable to any subject. "Patient" and "subject" are synonyms, and are used interchangeably. As used herein, they mean any animal (e.g. a mammal on which the inventions described herein may be practiced. Neither the term "subject" nor the term "patient" is limited to an animal under the care of a physician.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

The above descriptions of illustrated embodiments of the methods or devices are not intended to be exhaustive or to be limited to the precise form disclosed. While specific embodiments of, and examples for, the methods or devices are described herein for illustrative purposes, various equivalent modifications are possible within the scope of the methods, or devices, as those skilled in the relevant art will recognize. The teachings of the methods or devices provided herein can be applied to other processing methods or devices, not only for the methods or devices described.

The elements and acts of the various embodiments described can be combined to provide further embodiments. These and other changes can be made to the device in light of the above detailed description.

In general, in the following claims, the terms used should not be construed to limit the methods or devices to the specific embodiments disclosed in the specification and the claims, but should be construed to include all processing devices that operate under the claims. Accordingly, the methods and devices are not limited by the disclosure, but instead the scopes of the methods or devices are to be determined entirely by the claims.

While certain aspects of the methods or devices are presented below in certain claim forms, the inventor contemplates the various aspects of the methods or devices in any number of claim forms. Accordingly, the inventors reserve the right to add additional claims after filing the application to pursue such additional claim forms for other aspects of the methods or devices.

What is claimed is:

1. A method of modulating a brain activity of a subject, comprising:

subjecting the subject to repetitive current or magnetic pulses, wherein the repetitive current or magnetic pulses have a pulse frequency at a first target frequency, and a pulse amplitude that is variable to approximate a sinusoidal signal comprising a second target frequency and a target amplitude; and receiving a non-EEG biological metric of the subject and setting the second target frequency at the non-EEG biological metric, or a harmonic or sub-harmonic of the non-EEG biological metric of the subject; thereby improving a physiological condition or a neuropsychiatric condition of the subject.

2. The method of claim 1, further comprising setting the first target frequency at the non-EEG biological metric, or a harmonic or sub-harmonic of the non-EEG biological metric.

3. The method of claim 1, further comprising receiving an intrinsic frequency within a specific EEG band of the subject and setting the first target frequency at the intrinsic frequency within the specified EEG band, or a harmonic or sub-harmonic of the intrinsic frequency within the specified EEG band.

4. The method of claim 1, comprising setting the second target frequency at an intrinsic frequency within the non-EEG biological metric.

5. The method of claim 1, comprising receiving an intrinsic frequency within an alpha band of an EEG of the subject and setting the first target frequency at the intrinsic frequency within the alpha band of the subject; and determining a resting heart rate of the subject and setting the second target frequency at the resting heart rate of the subject.

6. The method of claim 1, wherein the value of the first target frequency is greater than the value of the second target frequency.

7. The method of claim 1, wherein the first target frequency is 10 Hz and the second target frequency is 1 Hz.

8. The method of claim 1, wherein subjecting the subject to repetitive current or magnetic pulses comprises subjecting the subject to current pulses and the current pulses are generated using transcranial alternating current stimulation.

9. The method of claim 1, wherein subjecting the subject to repetitive current or magnetic pulses comprises subjecting the subject to magnetic pulses and the magnetic pulses are generated using repetitive transcranial magnetic stimulation.

10. The method of claim 1, wherein the neuropsychiatric condition is any one or more of Autism Spectrum Disorder (ASD), Alzheimer's disease, ADHD, schizophrenia, anxiety, depression, coma, Parkinson's disease, substance abuse, bipolar disorder, a sleep disorder, an eating disorder, tinnitus, traumatic brain injury, post-traumatic stress syndrome, or fibromyalgia.

11. The method of claim 1, wherein the subjecting the subject to repetitive current or magnetic pulses comprises:

providing a device for applying a varying magnetic field, having:

a. a sine-wave generator which creates a sinusoidal signal having a sinusoidal amplitude and sinusoidal frequency, b. a pulse timing generator which creates a pulse timing signal having a pulse frequency, c. a driver circuit configured to provide a voltage or current output at an amplitude that is proportional to the sinusoidal amplitude at a time specified by the pulse frequency, and d. a magnetic field generator which generates a magnetic field with an amplitude proportional to the current or voltage output from the driver circuit;

subjecting the subject to repetitive magnetic pulses with the magnetic field generator of the device.

12. The method of claim 1, wherein the subjecting the subject to repetitive current or magnetic pulses comprises:

providing a device for applying a varying current, having:

a. a sine-wave generator which creates a sinusoidal signal having a sinusoidal amplitude and sinusoidal frequency, b. a pulse timing generator which creates a pulse timing signal having a pulse frequency, c. a driver circuit configured to provide a voltage or current output at an amplitude that is proportional to the sinusoidal amplitude at a time specified by the pulse frequency, and d. two electrodes, which are configured to provide electric current or voltage to the head of the subject with an amplitude proportional to the current or voltage output from the driver circuit;

subjecting the subject to repetitive current pulses with the two electrodes of the device.

13. A device for applying a varying magnetic field to a head of a subject, the device comprising:

a. a sine-wave generator which creates a sinusoidal signal having a sinusoidal amplitude and sinusoidal frequency; and b. a pulse timing generator which creates a pulse timing signal having a pulse frequency, wherein the pulse frequency is an intrinsic frequency within an alpha band of the subject, and the sinusoidal frequency is a resting heart rate of the subject; and c. a driver circuit configured to provide a voltage or current output at an amplitude that is proportional to the sinusoidal amplitude at a time specified by the pulse frequency; and d. a magnetic field generator which generates a magnetic field with an amplitude proportional to the current or voltage output from the driver circuit.

14. The device of claim 13, wherein the pulse frequency and the sinusoidal frequency are fixed values and the value of the pulse frequency is greater than the value of the sinusoidal frequency.

15. The device of claim 14, wherein the value of the pulse frequency is 10 Hz and the value of the sinusoidal frequency is 1 Hz.

16. A device for applying a varying electric current to a head of a subject, the device comprising:

a. a sine-wave generator which creates a sinusoidal signal having a sinusoidal amplitude and sinusoidal frequency; and b. a pulse timing generator which creates a pulse timing signal having a pulse frequency, wherein the pulse frequency is an intrinsic frequency within an alpha band of the subject, and the sinusoidal frequency is a resting heart rate of the subject; and c. a driver circuit configured to provide a voltage or current output at an amplitude that is proportional to the sinusoidal amplitude at a time specified by the pulse frequency; and d. two electrodes, which are configured to provide electric current or voltage to the head of the subject with an amplitude proportional to the current or voltage output from the driver circuit.

17. The device of claim 16, wherein the pulse frequency and the sinusoidal frequency are fixed values and the value of the pulse frequency is greater than the value of the sinusoidal frequency.

18. The device of claim 16, wherein the value of the pulse frequency is 10 Hz and the value of the sinusoidal frequency is 1 Hz.

* * * * *